United States Patent [19]

Zwanenburg et al.

[11] Patent Number: 5,250,155
[45] Date of Patent: Oct. 5, 1993

[54] PROCESS FOR REFINING SOAP-CONTAINING CRUDE POLYOL FATTY-ACID POLYESTER REACTION PRODUCTS

[75] Inventors: Arend Zwanenburg, Vlaardingen; Bart Barmentlo, Delft, both of Netherlands

[73] Assignee: Van den Bergh Foods Co., Division of Conopco, Inc., Lisle, Ill.

[21] Appl. No.: 626,919

[22] Filed: Dec. 13, 1990

[30] Foreign Application Priority Data

Dec. 21, 1989 [EP] European Pat. Off. ........ 89203310.1

[51] Int. Cl.⁵ .......................... B01D 3/34; C07H 1/00
[52] U.S. Cl. .......................... 203/34; 203/36; 203/37; 203/DIG. 6; 536/119; 536/127; 554/175
[58] Field of Search .................. 203/34, 35, 36, 37, 203/DIG. 6, 92, 95; 536/63, 119, 127; 554/168, 175

[56] References Cited

U.S. PATENT DOCUMENTS

| | | | |
|---|---|---|---|
| 2,948,717 | 8/1960 | Babayan | 536/119 |
| 3,963,699 | 6/1976 | Rizzi | 536/119 |
| 4,032,702 | 6/1977 | James | 536/119 |
| 4,334,061 | 6/1982 | Bossier, III | 536/119 |
| 4,517,360 | 5/1985 | Volpenhein | 536/119 |
| 4,518,772 | 5/1985 | Volpenhein | 536/119 |
| 4,611,055 | 9/1986 | Yamamoto | 536/119 |
| 4,968,791 | 11/1990 | Vander Plank | 536/119 |

FOREIGN PATENT DOCUMENTS

| | | |
|---|---|---|
| 0319091 | 6/1989 | European Pat. Off. . |
| 0319092 | 6/1989 | European Pat. Off. . |
| 0320043 | 6/1989 | European Pat. Off. . |
| 0256585 | 9/1989 | European Pat. Off. . |
| 0323670 | 12/1989 | European Pat. Off. . |

Primary Examiner—Virginia Manoharan
Attorney, Agent, or Firm—Gerard J. McGowan, Jr.

[57] ABSTRACT

A process for refining soap-containing crude polyol fatty-acid polyester reaction product, the process including one or more high-temperature refining treatments and as the first step in the refining process, contacting the crude reaction product with an acid to substantially convert the soap into its corresponding free fatty acids, and the subsequent step of substantially removing from the crude reaction product any salts therein prior to said one or more high-temperature refining treatments.

7 Claims, No Drawings

PROCESS FOR REFINING SOAP-CONTAINING CRUDE POLYOL FATTY-ACID POLYESTER REACTION PRODUCTS

The present invention relates to a process for refining soap-containing crude polyol fatty-acid polyester reaction products, and in particular, although not exclusively, crude sugar fatty-acid polyester reaction products.

Polyol fatty-acid polyesters and in particular, the sugar fatty-acid polyesters such as e.g. the sucrose fatty-acid polyesters, are known as suitable low-calorie fat-replacers in edible products. Substantially indigestible for human beings they have physical and organoleptic properties very similar to triglyceride oils and fats conventionally used in edible products. In addition, polyol fatty-acid polyesters are reported to have use as pharmaceutical agents e.g. in view of their ability to take up fat-soluble substances, such as in particular cholesterol, in the gastro-intestinal tract, and subsequently remove these substances from the human body.

In this specification the term "polyol" is intended to include any aliphatic or aromatic compound which comprises at least four free hydroxyl groups. Such polyols in particular include the group of sugar polyols, which comprises the sugars, i.e. the mono-, di- and polysaccharides, the corresponding sugar alcohols and the derivatives thereof having at least four free hydroxyl groups. Examples of sugar polyols include glucose, mannose, galactose, xylose, fructose, sorbose, tagatose, ribulose, xylulose, maltose, lactose, cellobiose, raffinose, sucrose, erythritol, mannitol, lactitol, sorbitol, xylitol and α-methylglucoside. A generally used sugar polyol is sucrose.

The term "polyol fatty-acid polyester" is intended to include any such polyesters or mixtures thereof of which, on an average, 70% or more of the polyol hydroxyl groups have been esterified with fatty-acids, i.e. which have degrees of esterification of 70% or more.

The term "fatty acid" refers to $C_8$–$C_{24}$ fatty acids which may be saturated or unsaturated, and may have straight or branched alkyl chains.

In general polyol fatty-acid polyesters are synthesized by a process in which a polyol, such as a mono- or disaccharide, is reacted with a fatty-acid lower alkylester, in general the fatty-acid methylester, in the presence of a transesterification catalyst, such as e.g. an alkali metal hydroxide or carbonate, and a soap emulsifier. In a first stage a polyol fatty-acid mono- or oligoester is formed, which in a second stage is further reacted with the fatty-acid lower alkylester to form polyesters of the desired degree of esterification. It is also possible to combine the two stages of the reaction into a single step.

Processes of this type have been described in e.g. the U.S. Pat. Nos. 3,963,699, 4,517,360, and 4,518,772, and EP patent specifications Nos. 0 256 585, 0 301 634 and 0 320 043.

The crude polyol fatty-acid polyester reaction products resulting from conventional syntheses contain in addition to the desired polyesters, components such as fatty-acid soaps, excess fatty-acid lower alkylesters and polyol fatty-acid oligoesters. Also, due to the relatively high temperatures at which conventional processes are carried out, often by-products are formed which may be undesirable in view of their chemical characteristics, such as in particular discolouring properties. In general it is therefore necessary to further purify or refine the crude polyol fatty-acid polyester reaction products resulting from such conventional syntheses.

The term "crude polyol fatty-acid polyester reaction products" is intended to refer to unrefined reaction products of processes for the synthesis of polyol fatty-acid polyesters. Such crude compositions in general contain of from 10 to 95% by weight of polyol fatty-acid polyesters, and in the case of syntheses aiming at substantially full esterification, the crude reaction products mostly contain of from 30 to 70% by weight of the polyol fatty-acid polyesters.

Conventional refining methods comprise a variety of different treatments including washings with water, organic solvents, acid or alkaline solutions, salting-out treatments, bleaching steps, distillation, stripping and deodorisation treatments.

U.S. Pat. No. 4,334,061 describes a process for the preparation of sucrose polyesters, in which the reaction product is washed using an aqueous alkaline solution of pH 7-12 in the presence of a polar organic solvent.

In EP 0 319 092 there is described a refining process avoiding the use of organic solvents, which is based upon a washing treatment using an aqueous alkaline solution of pH above 12.5.

In EP 0 319 091 it has been recognised that it is important to reduce the level of alkali metal ions before subjecting the crude polyol fatty-acid polyester product to subsequent high-temperature refining treatments such as stripping and deodorising. To avoid discolouring effects alkali metal ion levels are reduced to below 5 ppm. Alkali-metal reduction techniques include water and alkaline washings, optionally followed by acid washings, and bleaching.

In many instances the first one or more steps of prior-art refining process consist of aqueous washing treatments, each followed by separating off the aqueous phase using settling or centrifuging methods. Apart from the effluent problems associated with a plurality of washing treatments and the undesirable accumulated reductions in overall yield of refined polyol fatty-acid polyester, in particular the first washing by which the bulk of the crystallised soap as well as amounts of the polyester product and the excess fatty-acid lower alkylester are removed, creates an unattractive effluent stream from which potentially valuable components are difficult or costly to recover or recirculate.

In U.S. Pat. No. 4,611,055 there is described a process for the production of sucrose fatty-acid polyesters which involves acidification of the crude reaction mixture and subsequent subjection to a molecular distillation treatment. Molecular distillation allows distillation at relatively low temperatures thereby allegedly avoiding severe discolouring effects. On a technical scale molecular distillation is not attractive in view of the very high cost.

It is now an object of the present invention to provide a refining treatment, in particular applicable to refining processes of soap-containing crude polyol fatty-acid polyester reaction products, by which very low soap levels are achieved and the discolouring problems during subsequent high-temperature refining steps which are associated with too high soap levels, are avoided.

It is a further object of the present invention to provide a refining treatment by which the unattractive effluent stream attached to an initial aqueous washing step can be avoided, and which does not have to rely on a sequence of many washing steps, or in the alternative, which when used in combination with such sequences, improves on the refining result thereof.

It is still a further object of the present invention to provide a refining treatment which does not involve the use of organic solvents.

It is still further object of the present invention to provide a refining treatment which does not involve steps prohibitive from a cost point of view when applied on a technical scale.

Accordingly, in its broadest aspects the present invention provides a process for refining soap-containing crude polyol fatty-acid polyester reaction product, the process including one or more high-temperature refining treatments and comprising, as the first step in the refining process, contacting the crude reaction product with an acid to substantially convert the soap into its corresponding free fatty acids, and the subsequent step of substantially removing from the crude reaction product any salts therein prior to said one or more high-temperature refining treatments.

In general the soap component which the present invention aims to remove in a very convenient way, will be present in the crude polyol fatty-acid polyester reaction product by reason of its use as the emulsifier system for the preceding synthesis reaction of the polyester. To a limited extent it may also be due to partial conversion to soap of the co-reactant, often a fatty-acid methylester, which functions as the fatty-acid source for the polyester.

The amount of acid used to establish conversion of the soap component to its free fatty acids in principle must be sufficient to substantially convert all of the soap present in the crude polyester product. However, it is also envisaged that it is possible to establish conversion to such degree that the small levels of soap still present in the acidulated reaction product are easily removable simultaneous with the further salts in the subsequent salt-removal step. Allowable remaining levels of soap in the acidulated product are equal or below 0.1% by weight.

The amount of acid will depend upon the level of the soap emulsifier system used in the synthesis reaction as well as the amounts of soap formed or introduced during the synthesis reaction. For reasons of cost it is preferred that the amount of acid is as close to the precise amount needed as technically feasible to establish full neutralising of all the soap present in the crude reaction product. Amounts of acid in excess over what is theoretically needed to fully neutralize the alkaline components in the crude polyester reaction product can be used without adverse effects on the present process, suitable such excess amounts being up to 50% or more, excess amounts in the range of 0 to 10% being preferred, the range of 0 to 5% being particularly preferred.

To ensure substantially full conversion of the soap to free fatty acids the strength of the acid must be such that the equilibrium of the conversion reaction lies substantially fully at the side of the free fatty acids. Contacting the crude reaction product with the acid which in general is effected by addition of an aqueous acid solution to the crude reaction product, therefore should normally result in pH-values below 7 and preferably below 6, the range of pH 3 to 5 being preferred most.

Within the above-described constraints of amount, strength and pH-value the type of acid used to establish the conversion of the soap component to its free fatty acids is not particularly critical. Suitably, both inorganic and organic acids can be used which in view of the important application of the polyol fatty-acid polyesters in food products preferably are food grade. Suitable inorganic acids are phosphoric acid and dihydrogen phosphoric acid alkali metal salts. Suitable organic acids include acetic, lactic, succinic and citric acid, the latter acid being preferred.

Preferably, a relatively concentrated aqueous acid solution is used. Suitable concentrations lie within the range of 25% by weight or more. To allow convenient removal of the salt resulting from the acid step, concentrated acid solutions of 40% to 85% are preferred, concentrations of 40 to 60% being preferred most.

In general the acidulated crude polyester product is agitated to ensure sufficient contact between the soap component of the crude product and the acid added.

In batch-wise operations contact times of less than one hour are normally sufficient. In particular, contact times lie within the range of 1 to 30 minutes, 3 to 15 minutes being preferred.

In continuous operations, e.g. where the acid is in-line dosed to the crude polyester product, contact times generally are less than about 3 minutes, in particular, less than about 1 minute, and can be as short as 5 to 30 seconds.

For obvious reasons the overall refining process in accordance with the present invention is carried out at a temperature above the melting temperature of the polyester product to be refined. Preferably the acid step is carried out at elevated temperature, in particular at a temperature of from 40° to 150° C., and most preferably at a temperature of from 60° to 110° C.

The conversion of soap to free fatty acids is best established while low amounts of water are caused to be present in the mixture of crude polyester product and acid, such amounts in general being introduced by way of the concentrated aqueous solution of the acid. Suitable amounts of free water, i.e. water not being dissolved in the polyester phase nor being present as crystal or bound water of further components in the reaction product, after the addition of the acid solution are within the range of 0.1 to 2% by weight of the reaction product, levels of 0.1 to 0.5% being preferred.

The acid step is followed by the step of substantially removing from the crude polyester reaction product any salts present therein, in general alkali-metal salts which together with the free fatty acids result from the soap conversion by the acid. The substantial removal of the salt may be effected by using conventional separation techniques, such as centrifuge or filtration techniques. Suitable filtration techniques may involve the use of filter-aids, such as e.g. cellulose.

In particular, when the salt is removed by way of filtration, it has been found that the removal of the salt, generally being the alkali metal salt of the acid used in the soap-conversion step, is improved if the water level in the acidulated reaction product resulting e.g. from the aqueous acid solution, is reduced to very low levels which preferably correspond to a system substantially without free water being present, i.e. all water being either dissolved in the polyester phase or being present as crystal or bound water of further components in the reaction product. Suitable such water levels are below 0.3% by weight, and preferably lie below 0.1 or even 0.05% by weight. This can be conveniently effected by subjecting the reaction product to appropriate drying conditions at elevated temperature and reduced pressure. This drying step may be carried out subsequent to or during the contact times discussed herein-before.

A very convenient method of reducing the water to very low levels, in particular for use in combination with filtration, is flash-drying by which the reaction product is passed into a low-pressure chamber and any water present is vaporised adiabatically. The heat needed for such evaporation is drawn from the reaction mixture and accordingly this method can be used for the simultaneous drying and cooling of the reaction mixture from the temperature of the acid step to well below 100° C., in particular 70° to 90° C. If flash-drying is used for simultaneous drying and cooling, the water level in the reaction mixture after the addition of the acid solution may be higher than described hereabove, in order to ensure sufficient cooling during the flash-drying process. Water levels of 2 to 5% by weight will ensure a cooling of about 20° to 50° C. which in general will avoid any further separate cooling step.

Prior to the removal of the salt components it may be particular convenient to first subject the acidulated crude polyester product to an absorption or bleaching treatment involving an adsorbent such as silica, activated carbon or bleaching earth, and to remove the salt and the spent adsorbent simultaneously in a single filtration step.

Suitably, the bleaching agents are added to the reaction product in amounts of 0.2 to 5% by weight and preferably in amounts of 0.5 to 3% by weight. Often very good results are obtained with amounts of 1 to 2% by weight.

It has further been found that the removal of the salt as also the colour and discolouring properties of the final refined polyester product are advantageously affected, if prior to the introduction of the acid in the soap conversion step first a relatively small amount of an aqueous alkaline solution is added to the crude polyester product which is subsequently neutralized by the acid simultaneous to the conversion of the soap component to its free fatty acid.

Within the constraint of avoiding or minimizing the risk of the formation of undesirable components the particular combination of source, volume and level of alkalinity is not very critical and can be any of the readily available alkaline materials, such as the alkali metal hydroxides, carbonates or silicates, generally at a level within the range of 0.1 to 6N, in particular, 0.2 to 4N, or even, 0.2 to 1 or 2.5N. The aqueous alkaline solution is suitably added to the crude polyester product in an amount of 0.5 to 5% by weight of the product. Preferably, some agitation is applied to improve the contact between the crude polyester product and the aqueous alkaline solution.

In a batch-wise operation contact times of between 1 and 10 minutes between the introduction of the aqueous alkaline solution and the introduction of the acid have been found sufficient. In a continuous operation contact times are generally shorter than 3 minutes, such as less than about 1 minute, and can be as short as 5 to 30 seconds.

The refining process according to the invention may further include conventional washing treatments subsequent to the acid step and salt removal step. Suitable washings include simple water washings with or without added electrolytes, and alkaline or acid washings as described in EP 0 319 092 herein incorporated by reference.

To fully enjoy the benefits of the refining process of the present invention it is however preferred to apply the acid step and the optional prior addition of an aqueous alkaline solution without subsequent washing steps.

Subsequent to the acid step and removal of the salt components the polyol fatty-acid polyester reaction product may be further treated using one or more conventional bleaching steps with suitable bleaching agents or adsorbents such as silica, activated carbon and/or bleaching earth. As described herein-before it may be particularly convenient to introduce the adsorbent or bleaching agent into the acidulated polyester reaction product before the removal therefrom of the salt, in which case the filtration step to remove the salt and the adsorbent or bleaching agent can be combined.

Subsequent to the optional adsorbent or bleaching step the resulting polyester reaction product is subjected to one or more high-temperature refining treatments to remove the free fatty acids formed in the soap-conversion step and any further volatile components. In such high-temperature refining treatments the polyester reaction product will be subjected to a treatment at a temperature of above 150° C., in particular 150° to 300° C. In general the high-temperature refining treatment will include a distilling step, preferably at a temperature of from 160° to 210° C., and optionally and preferably a further deodorizing step, such as steam-stripping, at a temperature of 180° to 240° C., in particular, 190° to 240° C., and preferably 220° to 240° C.

Although the process according to the invention is suitable for refining crude products of the general group of polyol fatty-acid polyesters as defined hereinbefore, it is particularly suitable for refining crude products comprising polyol fatty-acid polyesters having degrees of esterification of 80% or more, or even 90% or more. In particular, such polyesters derived from the sugar polyols selected from the group of disaccharides or the alcohol derivatives thereof, such as sucrose, and esterified to over 95% fatty-acid substitution, are suitably refined by the process in accordance with the present invention.

Having a reduced risk of discolouring the polyol fatty-acid polyesters refined in accordance with the process of the present invention are particularly suitable to replace fully or partially conventional triglyceride fats in food compositions intended for high-temperature purposes, such as baking and frying oils. Generally, in such food compositions at least 10% by weight of the conventional triglyceride fat is replaced by the polyol fatty-acid polyesters in accordance with the present invention. Preferably, at least 50% of the conventional fat is replaced by the polyesters.

The invention is now further illustrated with reference to the following examples, percentages being by weight unless indicated otherwise.

EXAMPLE 1

A typical batch of 520 grams of crude sucrose fatty-acid polyester reaction product, synthesized in a solvent-free transesterification reaction between sucrose and touch-hardened soybean oil derived fatty-acid methylester to a degree of esterification of over 95%, consisted of the following components:

| | |
|---|---|
| sucrose fatty-acid polyester | 44.6% |
| fatty-acid methylester | 46.9% |
| soap (mainly coconut-derived potassium soap) | 3.8% |

| minor components | 4.7% |
|---|---|

This batch was first heated to a temperature of 80° C. While stirring at 800 rpm 11.5 grams of a 85% phosphoric acid solution was added, and stirring was continued for 15 minutes. Subsequently, the mixture was centrifuged for 10 minutes at 80° C. and 3000 rpm leaving 516 grams of substantially soap-free reaction product characterised by an elementary analysis of Na-3.4, K-88 and P-211 ppm.

After drying at 90° C. and 1 mbar and again increasing pressure to atmospheric level, the reaction product was subjected to a bleaching treatment at 90° C. involving a first addition of 0.2% of water followed by addition of 2% of acid-activated carbon. For 30 minutes this mixture was stirred at atmospheric pressure, followed by 30 minutes at reduced pressure (50 mbar). Subsequently, the bleached product was filtrated over a filter having an average pore size of 2 microns. Elementary analysis of the resulting product showed: Na-0.08 ppm, K-0.16 ppm and P<2 ppm. The colour values of the product as measured in a 2" cell of an Automatic Colori Meter ex Morgan Smith Electronics Ltd ® were 17.5 Yellow and 2.5 Red.

The bleaching step was repeated to give an elementary analysis of Na<0.05 ppm, K<0.05 ppm and P<2 ppm, and colour values (2" cell) of 12.0 Yellow and 1.7 Red.

The twice-bleached product was subsequently distilled and deodorised for a period of 3 hours at 200° C. and 1 mbar pressure to yield 212 grams of refined sucrose fatty-acid polyester (91.5% of theoretical yield) characterised by colour values (2" cell) of 22.5 Yellow and 3.0 Red.

EXAMPLE 2

To 500 grams of a batch of crude sucrose fatty-acid polyester reaction product having the same compositions as in example 1, and heated to temperature of 90° C., was added 20 ml of a 0.8N NaOH solution. After 5 minutes of stirring at 600 rpm, 10.7 ml of a 50% phosphoric acid solution was added, and stirring was continued for 30 minutes. Subsequently, 5 grams of acid-activated carbon was added, followed by 40 minutes of drying at a reduced pressure of 50 mbar, a temperature of 90° C. and stirring at 1900 rpm. Having continued the bleaching for a further 30 minutes the product was then filtrated over a filter having an average pore size of 2 microns. At this point of time the product contained 4.3% free fatty acids. The colour values of the product as measured in a 2" cell were 16.0 Yellow and 2.7 Red.

The resulting product was then subjected to a distillation for one hour at 200° C. to remove the bulk of the fatty-acid methylester (the level of remaining volatiles was about 5%). The product then contained about 0.5% of free fatty acids and showed colour values (2" cell) of 39 Yellow and 5.6 Red.

To the distilled product was then added 1% of bleaching earth (Supreme FF ex Tonsil ®). After stirring at 600 rpm, 90° C. and atmospheric pressure for 60 minutes, the product was filtrated over a filter (2 microns pore size), the filtrated product being characterised by colour values of 19 Yellow and 3.1 Red.

Finally, the product was steamed at 200° C. and 1 mbar pressure for 2 hours. The refined sucrose fatty-acid polyester product was characterised by colour values (2" cell) of 28 Yellow and 4.3 Red.

EXAMPLE 3

Up to the distillation step the experiment of example 2 was repeated on pilot-plant scale.

120 kg of a batch of crude sucrose fatty-acid polyester reaction product having the same compositions as in example 1, and heated to a temperature of 90° C., was added 4.8 liters of a 0.8N NaOH solution. After 5 minutes of stirring at 100 rpm, 4.0 kg of a 50% phosphoric acid solution was added, and stirring was continued for 15 minutes. Subsequently, 1.5 kg of acid-activated carbon was added, followed by 90 minutes of drying at a reduced pressure of 50 mbar, a temperature of 90° C. and continued. Having continued the bleaching for a further 30 minutes, the product was then filtrated over a filter having an average pore size of 10 microns. At this point of time elementary analysis showed Na<0.05 ppm and K−0.08 ppm, and colour values of the product as measured in a 2" cell were 18 Yellow and 2.8 Red.

The resulting product was then subjected to a distillation for one hour at 200° C. to remove the bulk of the fatty-acid methylester (the level of remaining volatiles was about 5%). At this point of time the product showed colour values (2" cell) of 38 Yellow and 5.3 Red.

To the distilled reaction product was then added 2 kg 2.4N NaOH solution at 90° C. and stirring at 100 rpm. After 5 minutes 0.6 kg of an aqueous 50% $H_3PO_4$ solution was added. While stirring the acidulated product was dried at 90° C. and 50 mbar pressure during 80 minutes. Subsequently, 970 grams of bleaching earth (Supreme FF ex Tonsil ®) was added and the bleaching continued at 90° C. and 50 mbar for 60 minutes. After filtration (10 microns filter) at 90° C. and 1.5 bar pressure the reaction product showed colour values of 18 Yellow and 2.5 Red (2" cell). Subsequent deodorising at 210° C. for 3 hours resulted in a refined sucrose fatty-acid polyester product having colour values of 19 Yellow and 2.6 Red (2" cell).

EXAMPLE 4

In order to investigate the effect of the addition of different levels and strengths of aqueous alkaline solution prior to the acid the following comparative experiment was carried out.

Batches of 500 grams of crude sucrose fatty-acid polyester reaction product, synthesized in a solvent-free transesterification reaction between sucrose and touch-hardened soybean oil derived distilled fatty-acid methylester to a degree of esterification of over 95%, consisted of the following components:

| sucrose fatty-acid polyester | 32.7% |
|---|---|
| fatty-acid methylester | 60.8% |
| soap (mainly coconut-derived potassium soap) | 3.3% |
| minor components | 3.2% |

These batches were first heated to 90° C. Subsequently, aqueous alkaline solutions of the type, level and strength as indicated in Table 1, were added. After 5 minutes of stirring at 600 rpm, to each of the batches a 50% phosphoric acid solution was added in amounts to neutralize the soap and the added alkaline solution (see Table 1). Stirring was continued for 15 minutes at 1900 rpm. Subsequently, to each of the batches 1% by weight of acid-activated carbon was added, followed by drying at a reduced pressure of 50 mbar and 600 rpm stirring. Having continued the bleaching after drying for a further 30 minutes, the products were filtrated over a filter having an average pore size of 10 microns.

The colour values of the various products as measured in a 2" cell of an Automatic Colori Meter ex Morgan Smith Electronics Ltd ® are indicated in Table 1 clearly showing the beneficial effect of the alkaline pre-treatment as also the particular suitability of the concentration strengths of about 0.8 to 4N.

Subsequently, the batches indicated with (a) and (b) in Table 1 are further refined by treatment with 2% by weight of acid-activated carbon. The suspension is stirred for 30 min (100 mbar, 90° C.) and filtered through a 2 microns filter, followed by deodorization at 200° C. and 1 mbar for 3 hours.

The colour values of the refined reaction products of batches (a) and (b) as measured in a 2" cell of an Automatic Colori Meter ex Morgan Smith Electronics Ltd ® are:

|  | Yellow | Red |
| --- | --- | --- |
| batch (a) | 18 | 2.9 |
| batch (b) | 10 | 1.6 |

TABLE 1

| aqueous alkaline solution | | | amount of 50% phosphoric acid | colour-values | |
| --- | --- | --- | --- | --- | --- |
| type | strength | level |  | red | yellow |
| — | — | — | 7.4 ml | 2.86 | 14.1 |
| NaOH | 0.8 N | 4.0% | 9.2 ml | 1.10 | 5.5 |
| NaOH | 1.6 N | 2.0% | 9.2 ml | 1.20 | 5.8 |
| NaOH | 4.0 N | 0.8% | 9.2 ml | 1.10 | 5.7 |
| NaOH | 4.0 N | 2.0% | 12.1 ml | 0.95 | 5.0 |
| NaOH | 8.0 N | 0.4% | 9.2 ml | 2.80 | 9.2 |
| $Na_2SiO_3$ | 0.8 N | 4.0% | 9.2 ml | 2.00 | 10.0 |

TABLE 1-continued

| aqueous alkaline solution | | | amount of 50% phosphoric acid | colour-values | |
| --- | --- | --- | --- | --- | --- |
| type | strength | level |  | red | yellow |
| $Na_2SiO_3$ | 1.6 N | 2.0% | 9.2 ml | 1.38 | 6.9 |
| $Na_2SiO_3$ | 4.0 N | 2.0% | 12.1 ml | 1.00 | 5.3 |
| $Na_2SIO_3$ | 4.0 N | 0.8% | 9.2 ml | 1.83 | 8.8 |

We claim:

1. A process for refining soap-containing crude polyol fatty-acid polyester reaction product avoiding discoloring problems during high temperature refining, the process comprising adding to the crude product 0.5 to 5% by weight of a 0.1 to 6N aqueous alkaline solution, contacting the alkali-added reaction product with an acid to substantially convert the soap into its corresponding free fatty acid and to neutralize the added alkali, then substantially removing from the crude reaction product salts therein, and subsequently, conducting at least one high temperature refining treatment selected from the group consisting of distillation and deodorization carried out at a temperature of from about 150° to 300° C.

2. The process of claim 1 in which the soap conversion step is carried out with an excess amount of the acid in the range of 0 to 10%.

3. The process of claim 1 in which the acid is selected from the group consisting of phosphoric acid, dihydrogen phosphoric acid alkali metal salts and citric acid.

4. The process of claim 1 in which the soap conversion step is carried out with a concentrated aqueous solution of the acid of within the range of 40 to 85% by weight.

5. The process of claim 1 in which the soap conversion step is carried out at a temperature of 40° to 150° C.

6. The process of claim 1 wherein the soap conversion step is carried out in the presence of from 0.1 to 2% by weight of free water.

7. The process of claim 1 in which the salt removal step is carried out by filtration, said crude reaction product having a water level before filtration below 0.3% by weight.

* * * * *